United States Patent [19]

Borden

[11] Patent Number: 4,812,664
[45] Date of Patent: Mar. 14, 1989

[54] APPARATUS FOR SCANNING A FLAT SURFACE TO DETECT DEFECTS

[75] Inventor: Peter G. Borden, Palo Alto, Calif.

[73] Assignee: High Yield Technology, Mountain View, Calif.

[21] Appl. No.: 119,762

[22] Filed: Nov. 12, 1987

[51] Int. Cl.⁴ .............................................. G01N 21/88
[52] U.S. Cl. ...................................... 250/572; 356/431
[58] Field of Search ............... 250/563, 572, 234, 235, 250/236; 356/429, 430, 431, 446

[56] References Cited

U.S. PATENT DOCUMENTS

| | | | |
|---|---|---|---|
| 2,947,212 | 8/1960 | Woods | 250/572 |
| 3,967,114 | 6/1976 | Cornillault | 250/572 |
| 4,162,126 | 7/1979 | Nakagawa et al. | 356/430 |
| 4,352,564 | 10/1982 | Roach | 250/572 |
| 4,595,289 | 6/1986 | Feldman et al. | 356/446 |

Primary Examiner—David C. Nelms
Assistant Examiner—William L. Oen
Attorney, Agent, or Firm—Skjerven, Morrill, MacPherson, Franklin & Friel

[57] ABSTRACT

A surface scanner useful for detecting defects on the surface of a water that is being processed in a vacuum equipment employs a light beam that scans the wafer surface in an arc. The scanning light beam impinges on the wafer surface at a low angle of incidence which permits the beam to pass under photosensing elements disposed in an arcuate array substantially congruous with the arc defined by the scanning light beam. The photosensing elements are patterned close to the wafer surface to receive light scattered by defects on the wafer surface.

10 Claims, 1 Drawing Sheet

APPARATUS FOR SCANNING A FLAT SURFACE TO DETECT DEFECTS

FIELD OF THE INVENTION

This invention relates to the detection of defects on a flat surface and in particular to a means for detecting small defects on the surface of a semiconductor wafer during manufacture of integrated circuits.

BACKGROUND OF THE INVENTION

Description of the Prior Art

During the manufacture of integrated circuits, vacuum equipment is generally used to process semiconductor wafers. Vacuum processing equipment, such as ion implanters, etchers, sputter coaters and chemical vapor deposition machines, are usually employed. During the processing and handling of the wafers along the production line, defects on the surface of the wafer can appear due to various conditions that occur in the equipment. For example, metal material may adhere to the wall of the sputter coater, the metal material can flake off the wall, and the flaked metal particles can land on the wafers. Any dust particles or contaminants that appear in the processing equipment tend to adhere to the wafer surface. As a result of the appearance of such undesirable particles on the wafer surface, short circuits or breaks in surface patterns are created which seriously degrade the performance of the finished integrated circuit.

It is highly desirable to detect such surface defects and to localize and control the sources of the problem in order to obtain optimum yields in the production of contamination-sensitive devices such as integrated circuits.

Various types of surface defects scanners have been described in the prior art. One type of surface scanner inspects surfaces of unpatterned wafers by using a focused laser beam that is scanned back and forth, so that the focus of the beam follows an arc. The wafer is moved in a direction perpendicular to the plane of the arc so that its surface is raster scanned. In such a system, which is described in the textbook "Silicon Processing For The VLSI Era, Volume I: Process Technology", by S. Wolf and R. N. Tauber, published by the Lattice Press, 1986, on page 514, seq. et., the moment arm of the arc is shown to be very long in order maintain the wafer surface within the depth of focus of the laser beam. The length of the moment arm causes the beam to be approximately normally incident to the wafer surface. Since the surface of the wafer is very flat, the laser beam will undergo specular reflection. If a surface defect is present, the reflected beam will scatter diffusely and the scattered light will be gathered by an optical collector and will be detected by a photomultiplier.

Another type of surface defect scanner employs a mercury-xenon arc lap to provide intense illumination over the entire surface of the wafer. A video camera that is off the axis of the light source will not see the light that is specularly reflected from the wafer surface, but will see light that is scattered from small defects.

Prior art surface defect scanners that use laser beams are characterized by depth of field problems. The prior art scanners employ a scanning light beam which traces an arc at its focal point. If the scanning beam which traces the arc is in a plane normal to the plane of the wafer surface, i.e., the angle of incidence $\beta$ equals 90°, then the focal point does not stay in the plane of the wafer surface but moves above and below the wafer surface. Therefore, the intensity of the light at the wafer surface will vary, because the sensitivity of the surface scanner is a function of the intensity of the light at the wafer surface. Prior art systems attempt to solve this problem by using a very long focal length which minimizes this undesirable deviation but provides a larger depth of field of the beam. As a result, the scanner system is made to be very large which in effect precludes its use in vacuum chambers with limited space.

The prior art systems are extremely large and bulky because there is a need to use a long focal length so that the arc traced by the scanning light is almost linear. In the system that employs a laser surface defects scanner, a scanning mirror is required to be positioned a large distance above the surface of the wafer. The large distance is determined by the requirement for the wafer surface to lie within the depth of focus of the laser spot across the full arc of the scan. The large depth of field thus necessitates a relatively large vacuum chamber.

Furthermore, in the system that uses an arc lamp, the apparatus must be large enough to accommodate the lamp and the lenses that are required to illuminate the wafer surface uniformly, and the viewing camera. Therefore, in view of the large size of the scanner equipment and incompatibility with vacuum chambers, prior art systems used for surface defect detection have not been installed in vacuum processing equipment.

SUMMARY OF THE INVENTION

It is highly desirable to incorporate a surface defect detector in a vacuum equipment that is characterized by vacuum compatibility and yet is relatively small and very compact.

In accordance with this invention, a surface defect scanner for use in a vacuum equipment comprises means for directing a scanning light beam to scan the surface of a wafer at an angle that allows photosensing means to be disposed closely adjacent to the surface of the wafer. The wafer is moved in a linear direction while the light beam oscillates back and forth and scans the surface in an arcuate scan path. If the surface of the wafer has defects or particles which interrupt the smoothness or flatness of the surface typography, the light that impinges on the wafer surface is scattered from those defective points. The elements of the photosensing means, which are very close to the wafer surface and collect a maximum amount of scattered light, are spaced sufficiently from the wafer surface so that they do not intercept the scanning light beam. By virtue of the compact design, the surface defects detector of this invention can easily be incorporated within a vacuum chamber to allow inspection of wafers in the vacuum environment where they are subject to contamination.

DESCRIPTION OF THE DRAWINGS

The invention will be described in greater detail with reference to the drawings in which.

DETAILED DESCRIPTION OF THE INVENTION

Figure 1:
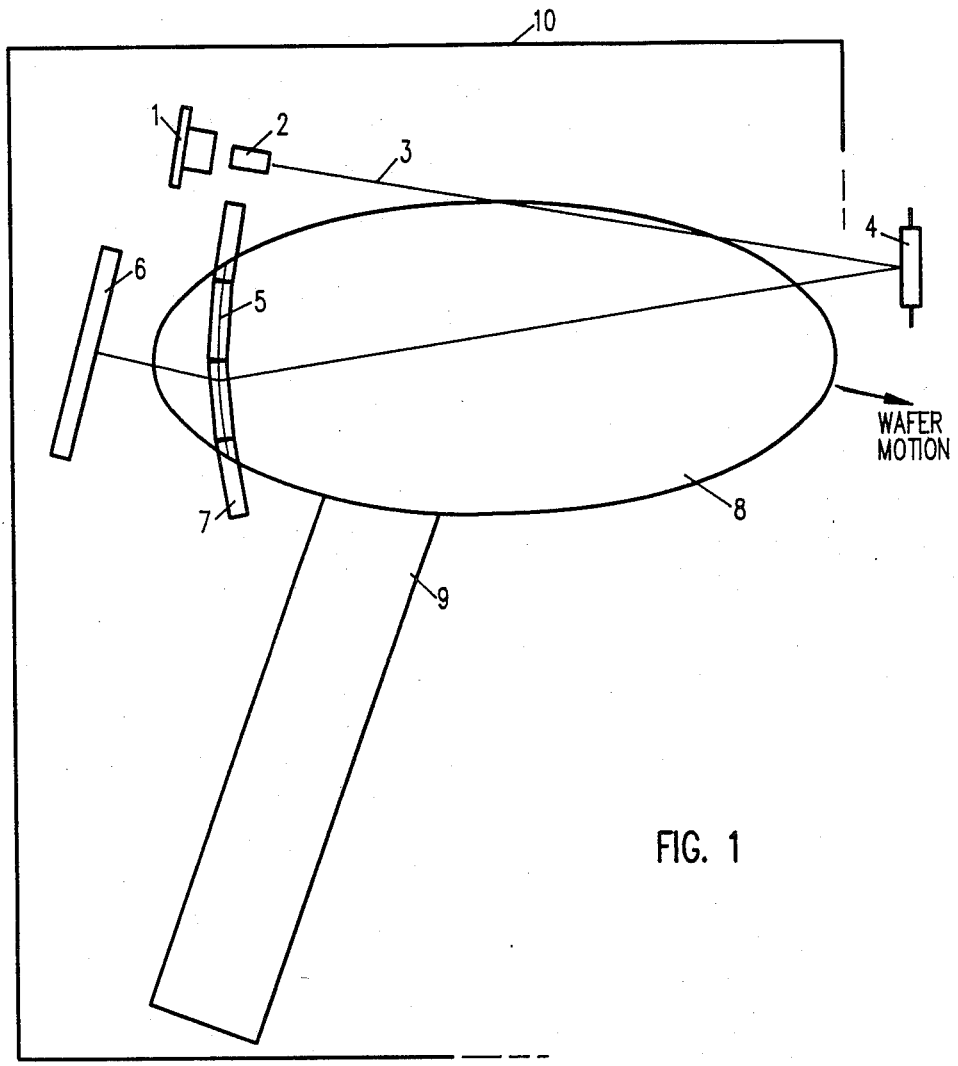
FIG. 1 is a representational view of the surface scanner, in accordance with this invention.

With reference to FIG. 1, a light source 1, which may be a solid state laser diode, such as an AlGaAs laser diode, provides a collimated beam 3. The beam 3 may be a 20 milliwatt beam having a wavelength of 780 nm, for example. The beam is directed through a focusing lens 2, which preferably is an 0.11 pitch gradient index rod lens. The beam is reflected off a scanning mirror 4 that scans the beam in an arc 5 defined across the surface of a wafer 8. The beam 3 is specularly reflected from the surface of the wafer and impinges on a beam stop 6 which does not allow the beam to be further reflected into the wafer area.

If a defect is present at any point where the light beam hits the surface of the wafer, the light will be scattered. The phenomenon of scattering light is described in the text book entitled *Light Scattering by Small Particles,* van de Hulst, published by Dover Publications, 1981, wherein the descriptive theory of Mie is presented. A series of photocells 7 are positioned in an arcuate array above the arc 5 defined by the scanning light beam. The photocells collect a significant amount of scattered light by virtue of being mounted very close to the surface of the wafer. However, the photocells are not in a position so that they can intercept the light beam which is directed to the wafer surface. The entire scanner chamber assembly is contained within the vacuum environment of a vacuum chamber, represented partially by the lines 10.

Figure 2:
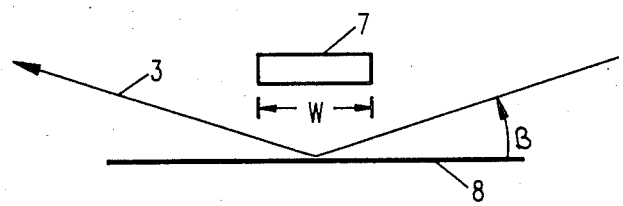
FIG. 2 is a representational side view illustrating partially the path of the light beam relative to a flat surface that is being scanned.

As shown in FIG. 2, if the angle that the incident beam makes with the surface of the wafer is defined as $\beta$, and the width of each photocell is W, then the minimum height for spacing the photocell from the surface of the wafer is $(W/2) \tan(\beta)$. In an implementation of this invention, the angle $\beta$ was about 10°, the width of the photocell was 1 centimeter, and the height of the photocells above the surface of the wafer was 0.5 cm.

By virtue of this invention, the depth of field can be virtually eliminated, thus allowing a system having a small and compact configuration. This is because the axis of the scan mirror 4 is perpendicular to the wafer surface, so that the focus traces an arc in the plane of the wafer, with no deviation out of that plane. In addition, the use of a shorter focal length system allows the use of a smaller size focal spot, thereby providing a higher laser power density at the wafer surface with increased sensitivity to smaller defects.

The light that is collected by the photocells 7 is amplified by an amplifier circuit (not shown) in a well known manner. Any electrical pulse that is generated as a result of the collected light is indicative that a defect is present on the surface of the wafer.

The scanning procedure is accomplished by the movement of the wafer on a handler arm 9 that transports the wafer in a substantially linear direction concurrently with the scanning of the beam along the arc 5. In effect, the wafer surface is scanned in a raster fashion in successive arcuate paths. If we assume the beam to be 50 microns in diameter at the wafer surface, and at an angle of incidence of 10°, and if the wafer is 15 centimeters in diameter, for example, then 520 scans will cover the surface of the wafer. A scan frequency in the range of 25-200 Hertz, preferably 50 Hertz, which is provided by the torsion mirror scanner 4, allows the wafer to be scanned in a little over 10 seconds.

It should be understood that the invention is not limited to the specific parameters, dimensions, angles and materials described herein. The novel configuration affords improvements in scan detection of surface defects in a compact space within a vacuum environment with higher detection sensitivity. Although the description is directed to semiconductor wafer processing, the invention is applicable to workpieces other than wafers where very flat surface topography without defects is desired.

What is claimed is:

1. A surface defect scanner apparatus for use in vacuum equipment comprising:
   means for moving a semiconductor wafer in a predetermined direction in a first plane defined by a surface of said wafer;
   a source comprising a solid state laser diode for providing a light beam;
   means for receiving said light beam from said source and for reflecting said light beam to said wafer, including means for scanning the surface of said wafer, said reflecting and scanning means comprising a scanning mirror for scanning the reflected beam in an arc across the surface of said wafer, said mirror having an axis disposed substantially perpendicular to said first plane so that the depth of field is virtually eliminated;
   the angle of incidence of said beam from said source onto said reflecting means and the angle of reflection of said beam from said reflecting means to said wafer being less than 60°;
   at least one photosensing element for detecting light scattered from the impingement of the reflected light beam on said wafer surface, the sensing surface of said element being at a relatively close height above said wafer, said height being in a second plane that is substantially parallel to said first plane and wherein said second plane is disposed between said first plane and said reflecting means.

2. A surface defect scanner apparatus as in claim 1, wherein said light beam source comprises an optical lens means for focusing said beam.

3. A surface defect scanner apparatus as in claim 2, wherein said solid state laser diode provides a collimated beam having a wavelength of approximately 780 nanometers.

4. A surface defect scanner apparatus as in claim 3, wherein said laser means comprises an AlGaAs laser diode.

5. A surface defect scanner apparatus as in claim 2, wherein said optical lens means comprises a gradient index rod lens.

6. A surface defect scanner apparatus as in claim 1, wherein said scanning mirror comprises a torsion mirror scanner having a scan frequency of approximately 25-200 Hertz.

7. A surface defect scanner apparatus as in claim 1, wherein said at least one photosensing element comprises a plurality of photocells that are positioned in an arcuate path, said arcuate path having substantially the same radius as the arcuate path defined by the scanning beam from said light beam reflecting means that impinges on said wafer.

8. A surface defect scanner apparatus as in claim 7, wherein the width of each photocell is defined by W, the angle of the incident beam relative to the wafer surface is $\beta$ and the minimum height of the photocell elements above the wafer surface is defined by (W/2) tan ($\beta$).

9. A surface defect scanner apparatus as in claim 1, including a beam stop positioned to receive the light beam that is reflected from the surface of the wafer.

10. A surface defect scanner apparatus as in claim 1, including a vacuum chamber for containing said light beam source, light beam receiving and reflecting means, scanning means, and said photosensing element in a vacuum environment.

* * * * *